(12) United States Patent
Alfano et al.

(10) Patent No.: US 6,280,386 B1
(45) Date of Patent: Aug. 28, 2001

(54) APPARATUS FOR ENHANCING THE VISIBILITY OF A LUMINOUS OBJECT INSIDE TISSUE AND METHODS FOR SAME

(75) Inventors: Robert R. Alfano, Bronx, NY (US); Stavros G. Demos, Livermore, CA (US); Wubao Wang, Flushing; Jamal Ali, Brooklyn, both of NY (US)

(73) Assignee: The Research Foundation of the City University of New York, New York, NY (US)

( * ) Notice: Subject to any disclaimer, the term of this patent is extended or adjusted under 35 U.S.C. 154(b) by 0 days.

(21) Appl. No.: 09/098,258

(22) Filed: Jun. 16, 1998

Related U.S. Application Data
(60) Provisional application No. 60/049,639, filed on Jun. 16, 1997.

(51) Int. Cl.[7] .................................................. A61B 5/00
(52) U.S. Cl. .................... 600/431; 600/476; 600/477; 600/478; 600/109
(58) Field of Search ................................. 600/431, 407, 600/473, 475–479, 109

(56) References Cited

U.S. PATENT DOCUMENTS

| | | | |
|---|---|---|---|
| 5,042,494 | * | 8/1991 | Alfano ................................. 600/478 |
| 5,678,550 | * | 10/1997 | Bassen et al. ........................ 600/431 |
| 5,823,942 | * | 10/1998 | Toida .................................... 600/477 |
| 5,827,190 | * | 10/1998 | Palcic et al. ......................... 600/476 |
| 5,853,370 | * | 12/1998 | Chance et al. ....................... 600/431 |

OTHER PUBLICATIONS

P. Stefan Anderson et al., "Multispectral System for Medical Fluorescence Imaging", IEEE, J. Quantum Electronics, QE–23, pp. 1798–1805, Oct. 1997.

K. M. Zoo et al., "Imaging objects hidden in scattering media using a fluorescence–absorption technique", Opt. Lett. 16, pp. 1252–1254, 1991.

\* cited by examiner

*Primary Examiner*—Ruth S. Smith
(74) *Attorney, Agent, or Firm*—Dilworth & Barrese, LLP

(57) ABSTRACT

Imaging of objects within tissue is enhanced by applying a contrast agent to a sample to be imaged to augment the emissions from an object, thereby forming a luminous object. The tissue is then illuminated and two image signals are recorded. The contrast agent is selected to bind to the object and provide spectral characteristics significantly different from that of the tissue for the two recorded image signals. The two image signals are subtracted to substantially minimize an image component resulting from the tissue and enhance an image component from the luminous object. The imaging methods and apparatus are particularly well suited for medical imaging where the object is diseased tissue such as tumors.

19 Claims, 16 Drawing Sheets

PRIOR ART $I(\lambda E, \lambda 1)$  $I(\lambda E, \lambda 2)$  $I(\lambda E, \lambda 2) - I(\lambda E, \lambda 1)$ (a)

(b)

(c)

$I(\lambda 1, \Delta\lambda)$ $I(\lambda 2, \Delta\lambda)$ $I(\lambda 2, \Delta\lambda) - I(\lambda 1, \Delta\lambda)$ (a)

(b)

(c)

θ : Rotation of mounting table around the sample

ω: Angle between directions of illumination and detection

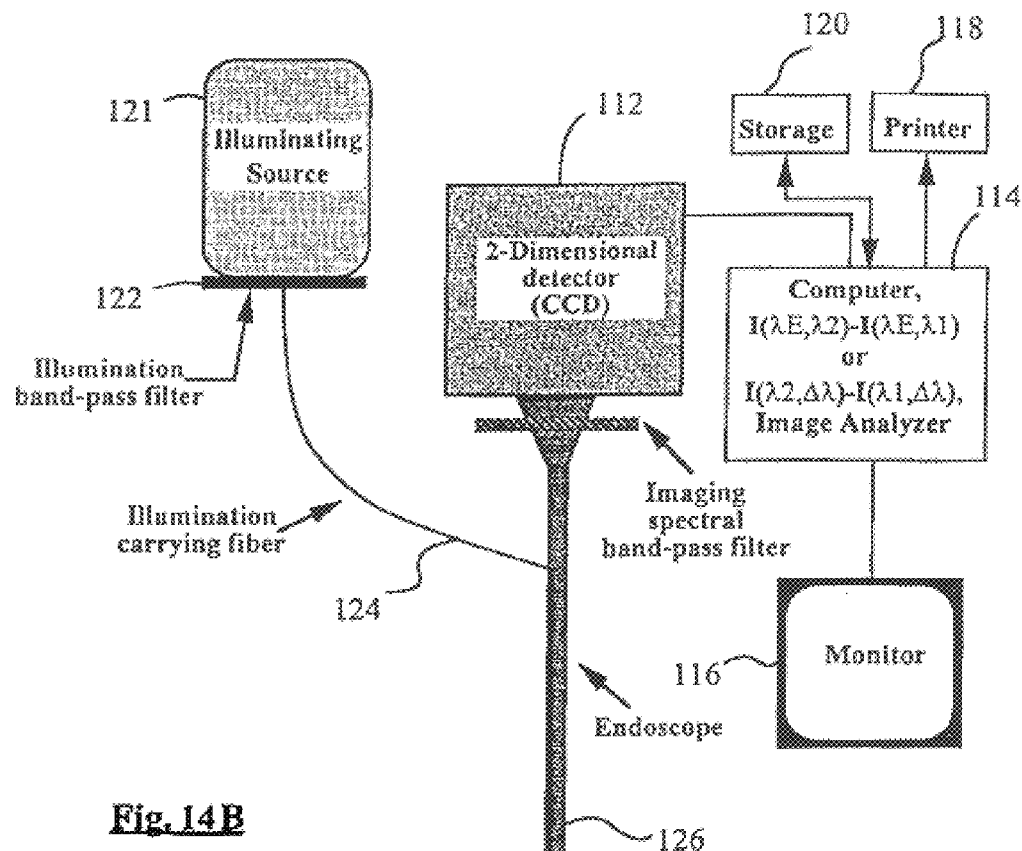
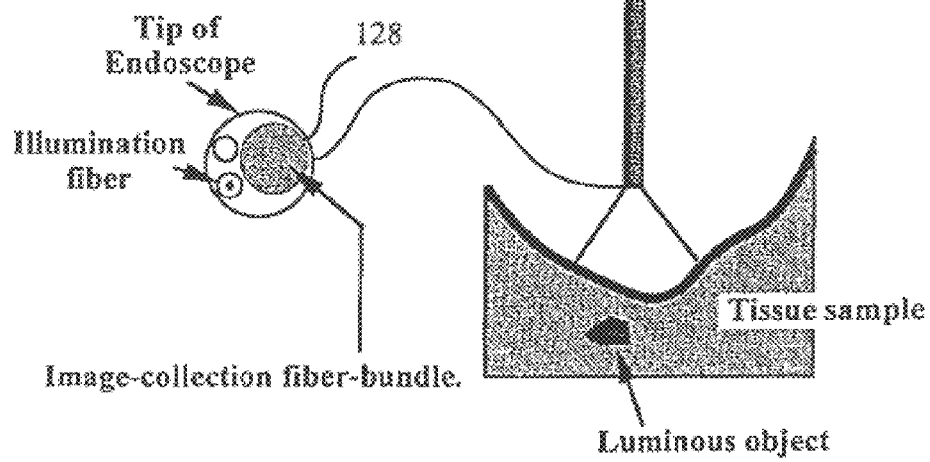
Fig. 14A
Fig. 14B

APPARATUS FOR ENHANCING THE VISIBILITY OF A LUMINOUS OBJECT INSIDE TISSUE AND METHODS FOR SAME

This application claims the benefit of United States Provisional Application, Ser. No. 60/049,639, filed on Jun. 16, 1997, entitled "Enhancement of Visibility of a Luminous Object Inside Human Tissue Using Emission and/or Excitation Spectral Difference Detection."

BACKGROUND OF THE INVENTION

1. Field of the Invention

The present invention relates generally to diagnostic imaging and more particularly relates to methods and apparatus for optical imaging of tissue containing a luminous object, such as a section of diseased tissue with an applied contrast agent.

2. Description of the Related Art

In many current modalities for medical imaging (i.e. X-ray, PGT, and CAT tomography), contrast agents have been used to enhance image quality and the resulting volume of information. Contrast agents have been introduced in optical imaging to enhance the ability to take an image of an object hidden in a scattering medium or tissue and improve the resulting image quality. An object located inside a scattering medium, such as tissue, is made luminous and viewed using its emission light by introducing a fluorescence dye or inorganic phosphorescence agent. Improvement in the image quality is achieved due to the fact that the distance that the emitted light by the luminous object traverses from the object to the exit point of the scattering medium is shorter than the distance that the illuminating light has to traverse in transillumination techniques. Further improvement of the image quality has been demonstrated by selectively reducing the diffusive component of the emitted light by the luminous object reaching the detector by introducing an absorbing dye into the random medium or using polarization difference imaging.

When tissue is illuminated with light, a first portion of the light undergoes elastic scattering, a second portion of the light undergoes inelastic scattering and a third portion of the light is absorbed by the tissue. When a tissue molecule absorbs a photon, it acquires an amount of energy that it will release within a time interval of less than 1 second. The excess energy of the photo excited tissue molecules is released via nonradiative processes giving rise to generation of phonons or via radiative processes giving rise to light emission by the tissue. FIG. 1A shows native light emission by breast chicken tissue illuminated with a 632 nanometer (nm) source. The emissions from the tissue extend up to 950 nm covering a significant part of the "spectral window" that may be used for optical biomedical imaging (700–1200 nm). The temporal profile of the emission shown in FIG. 1A is shown in FIG. 1B. The temporal profile extends to over 2 nanoseconds showing that the recorded light is due to emission by photo excited tissue molecules without any contrast agents.

Contrast agents for use in medical imaging are specifically selected to bind to molecules associated and/or involved in tumors, cancers, brain disorders, liver disorders or other disorders or diseases of the human body. The contrast agents may be injected into the human body to reach and concentrate mostly in the diseased part of the body. Optical images of the diseased part of the human body may then be attained provided that the diseased part of the body can be illuminated and the emitted light from the contrast agent can be recorded by a detection/imaging system.

When the concentration of the contrast agent located at the diseased part of the human body is very small (giving rise to very weak emission) or when the object is deep inside the tissue and it is difficult to illuminate and/or record the emitted light (due to the thickness of the tissue between the diseased tissue and the exterior of the tissue), the detection of the emitted light by the luminous object may be orders of magnitude less than the emitted native fluorescence light by the normal tissue. This effect makes the detection of the emission from the diseased part of the body very difficult or impossible.

Therefore, there remains a need for apparatus and methods that address these problems and enhance the visibility of a luminous object inside a sample of tissue.

SUMMARY OF THE INVENTION

In accordance with a first embodiment of the present invention, an imaging system which enhances the visibility of a luminous object located inside tissue is formed. The imaging system includes means to illuminate the tissue; means to detect a first image signal and a second image signal of the luminous object; and means to perform normalization and subtraction of said recorded image signals, whereby a new image signal is generated in which an image of the luminous object is enhanced.

In accordance with a first imaging method, a selected contrast agent is applied to a tissue specimen to be imaged. The tissue specimen is then illuminated with a light source operating a selected wavelength. Images are then recorded at a first imaging wavelength and at least a second imaging wavelength. The recorded images are then subtracted from one another to minimize the image component resulting from the tissue specimen and enhance an image component resulting from a luminous body within the tissue specimen.

The first and the second imaging wavelengths are preferably selected such that the emission characteristics of the tissue are substantially constant while the emission characteristics of the illuminated body change significantly.

In accordance with another imaging method of the present invention, a selected contrast agent is applied to a tissue specimen to be imaged. The tissue specimen is then illuminated with a light source operating at a first illumination wavelength and at least a second illumination wavelength. First image signals, resulting from excitation by the first illumination wavelength, and second image signals, resulting from excitation by the second illumination wavelength, are then recorded at a selected imaging bandwidth. The recorded image signals are then subtracted from one another to minimize an image component resulting from the tissue specimen and enhance an image component resulting from a luminous body within the tissue specimen.

The first and the second illumination wavelengths are preferably selected such that the absorption characteristics of the tissue are substantially constant while the emission characteristics of the illuminated body change significantly.

These and other objects, features and advantages of the present invention will become apparent from the following detailed description of illustrative embodiments thereof, which is to be read in connection with the accompanying drawings.

BRIEF DESCRIPTION OF THE DRAWINGS

The invention will be described in detail in the following description of preferred embodiments with reference to the following figures, wherein:

FIGS. 5A, 5B and 5C are diagrams of simulated images a sample, wherein FIG. 5A is an image at $I(\lambda_E, \lambda 1)$, FIG. 5B is an image at $I(\lambda_E, \lambda 2)$, and FIG. 5C is a resulting image of after subtraction and normalization of the images from FIGS. 5A and 5B;

FIGS. 6A, 6B and 6C are exemplary images of a sample, wherein FIG. 6A is an image recorded at $I(\lambda_E, \lambda 1)$, FIG. 6B is an image recorded at $I(\lambda_E, \lambda 2)$, and FIG. 6C is a resulting image of a luminous object after subtraction and normalization of the images from FIGS. 6A and 6B;

FIGS. 9A, 9B and 9C are diagrams of simulated images of a sample illuminated with light of wavelengths $\lambda_1$ and $\lambda_2$, wherein FIG. 9A is an image at $I(\lambda_1, \Delta\lambda)$, FIG. 9B is an image at $I(\lambda_2, \Delta\lambda)$, and FIG. 9C is a resulting image after subtraction and normalization of the two images, $I(\lambda_2,\Delta\lambda)-I(\lambda_1,\Delta\lambda)$.

FIGS. 10A, 10B and 10C are exemplary images of a sample illuminated with light of wavelengths $\lambda_1$ and $\lambda_2$, wherein FIG. 10A is an image recorded at $I(\lambda_1, \Delta\lambda)$, FIG. 10B is an image recorded at $I(\lambda_2, \Delta\lambda)$, and FIG. 10C is a resulting image of a luminous object after subtraction and normalization of the two images, $I(\lambda_2,\Delta\lambda)-I(\lambda_1,\Delta\lambda)$.

FIG. 14A is a pictorial diagram of an apparatus for imaging a luminous object located inside tissue using an endoscope, the apparatus being formed and operated in accordance with the present invention;

FIG. 14B is a cross sectional view of an endoscope used in the apparatus of FIG. 14A;

FIG. 15B is a cross sectional view of an imaging probe used in the apparatus for imaging a prostate of FIG. 15A.

DETAILED DESCRIPTION OF PREFERRED EMBODIMENTS

Figure 2:
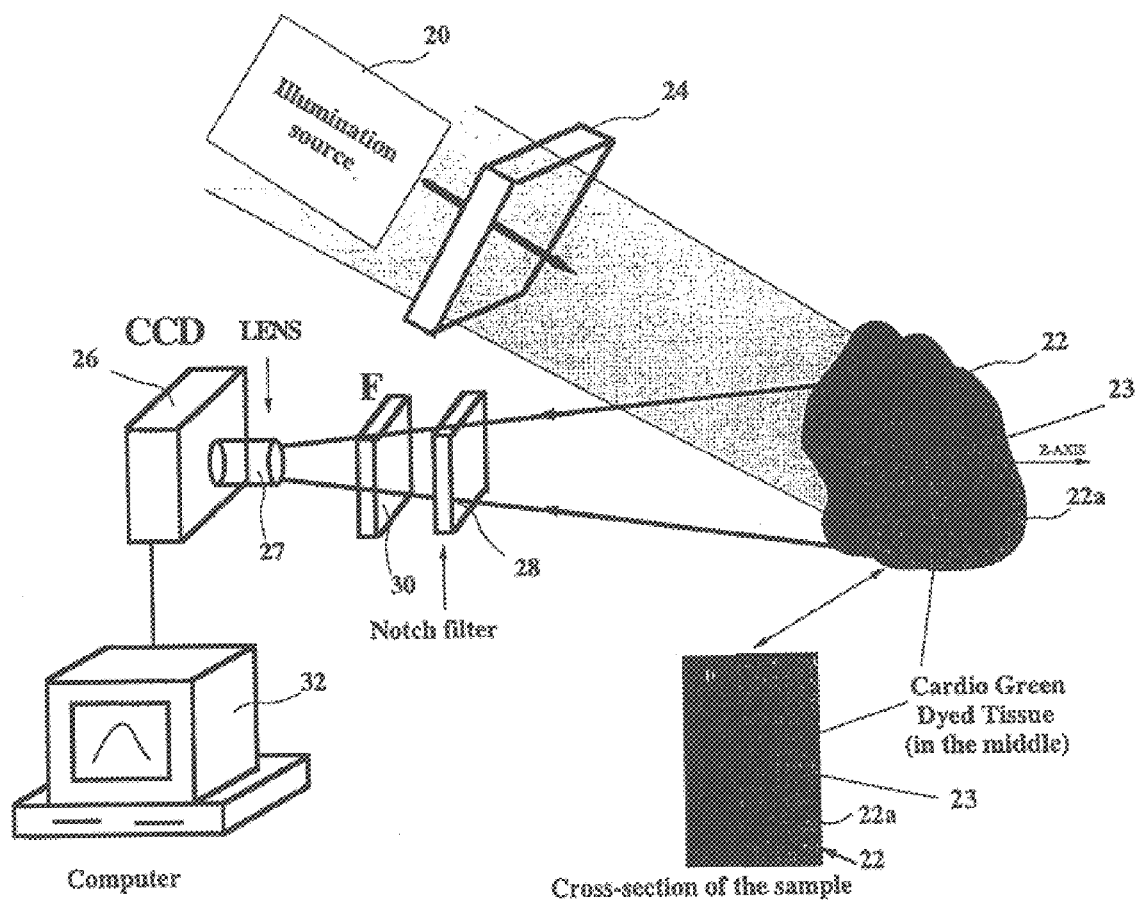
FIG. 2 is a simplified block diagram of an apparatus for optical imaging of a luminous object inside tissue formed and operating in accordance with the present invention.

FIG. 2 is a simplified block diagram illustrating a basic system for performing optical imaging in accordance with the present invention. The system includes an illumination source 20 which is used to illuminate a sample 22. In FIG. 2, the sample is a body of tissue 22A with a lesion 23, which when subjected to a contrast agent becomes an efficient luminous object.

The illumination source 20 provides substantially monochromatic light at a wavelength selected in accordance with a method of the present invention in view of the tissue being sampled and the contrast agent being employed. An exemplary illumination source 20 includes a dye laser, tunable in the 570–635 nm and 690–780 nm spectral region using R6-G and Pyridine 1 dyes, respectively. The laser beam is expanded to a 15 cm diameter beam and then passed through a 5 cm diameter aperture. This allows only the central portion of the collimated beam to illuminate the sample 22, thereby providing moderately uniform illumination of the sample 22. A narrow-band laser-line interference filter 24 is preferably interposed between the illumination source 20 and the sample 22 to ensure substantially monochromatic illumination of the sample.

The system of FIG. 2 further includes a detector 26, preferably including suitable optics 27 to capture an image from the sample 22 in the back scattering geometry. The detector 26 preferably takes the form of a CCD camera with the optics 27 taking the form of a 50 mm lens. A laser-line notch filter 28 is included and is interposed between the sample 22 and the detector 26 to exclude any back scattered illumination light. A second filter 30 (narrow band filter) follows the notch filter 28 and is used to select the desired spectral wavelength of the emitted light by the sample to record the image. The properties of filters 28 and 30 are selected based on the illumination wavelength, tissue characteristics, selected contrast agent and selected imaging wavelengths. When the selected contrast agent is cardio green dye, filter 30 takes the form of a 790 nm and/or 830 nm narrow band interference filter(s) for a first imaging method (referred to as emission spectral difference imaging). For a second imaging method (referred to as excitation spectral difference imaging), filter 30 takes a form of a RQ830 long pass filter associated with the 710 nm and/or 760 nm narrow band filter used for filter 24. Signals from the detector 26 are presented to an imaging processing and display system 32 formed and operating in accordance with the present invention.

Figure 1:
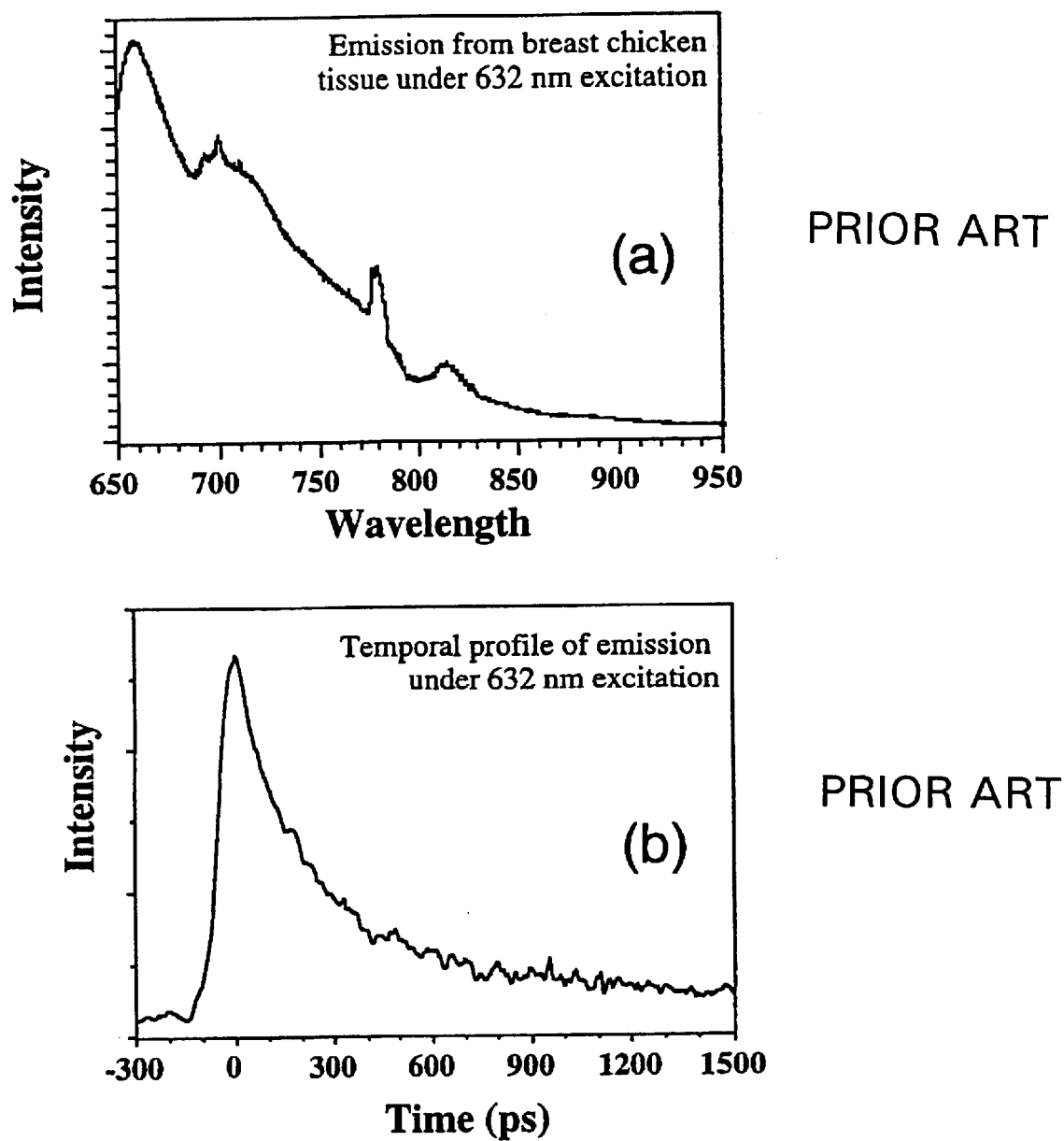
FIGS. 1A and 1B are graphs illustrating an emission spectral profile and temporal spectral profile, respectively, of a sample breast chicken tissue subjected to 632 nm illumination.
Figure 3A:
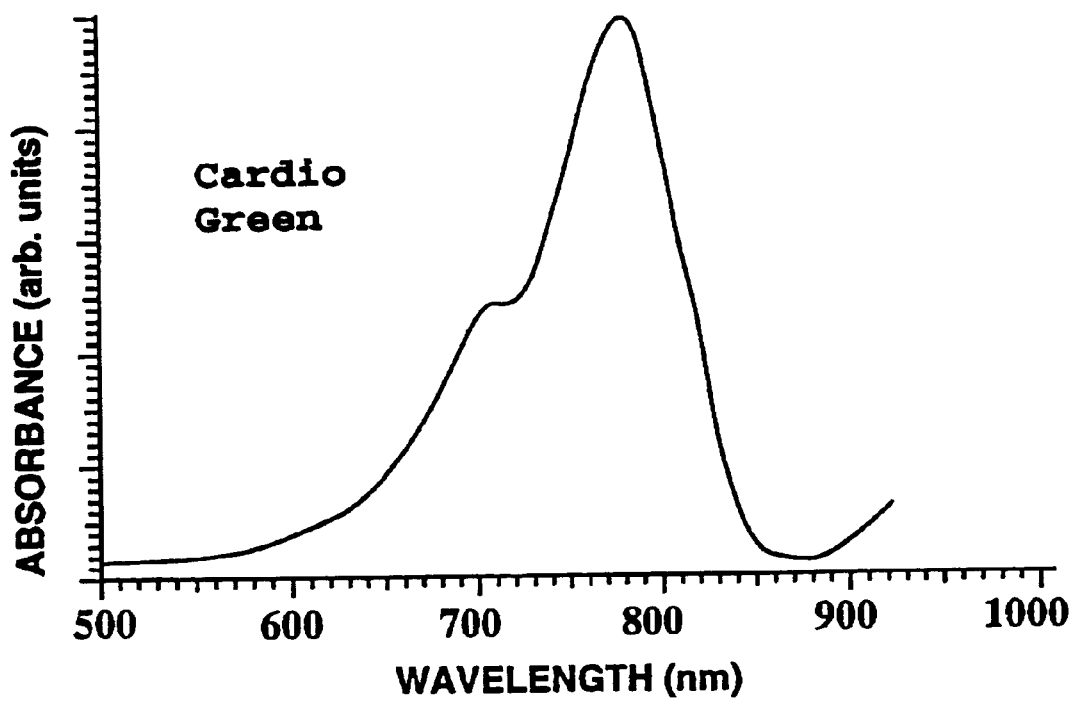
FIGS. 3A and 3B are graphs illustrating spectral profiles, and more particularly illustrating absorption versus wavelength and fluorescence versus wavelength respectively, of cardio green dye used as an exemplary contrast agent for the imaging methods of the present invention.
Figure 3B:
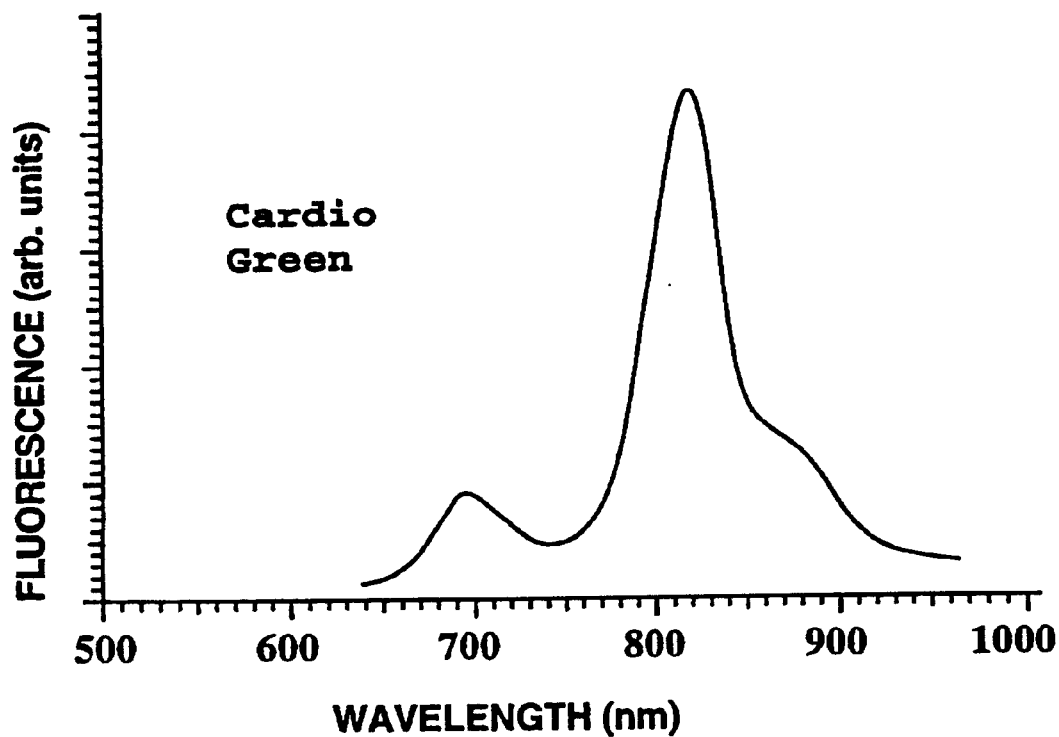

The spectral profile of the emissions from an exemplary tissue sample (breast tissue from a chicken) subjected to 632 nm excitation is shown in FIG. 1. It is expected that the absorption by the tissue is approximately the same in the 700–1100 nm spectral region. The absorption and emission spectral profiles of the cardio green dye used as an exemplary contrast agent are illustrated in FIGS. 3A and 3B respectively. Referring to FIG. 3A, the cardio green dye absorption band starts at about 600 nm and peaks at about 780 nm. Referring to FIG. 3B, the emission profile peaks at 820 nm and extends beyond 950 nm. Cardio green dye is but one exemplary contrast agent. Different contrast agents with similar spectral properties can be selected which exhibit specific binding properties to different molecules in different organs (i.e., breast, liver, brain, kindly, prostate, pancreas). Detection of the image characteristics of such tissues stained with suitable contrast agent dyes will help to highlight and diagnose different diseases such as Huntington's disease, Alzheimer's disease, epilepsy, diabetes, and tumors in breasts, liver, brain, kindly, glands, pancreas, and prostate.

Figure 4:
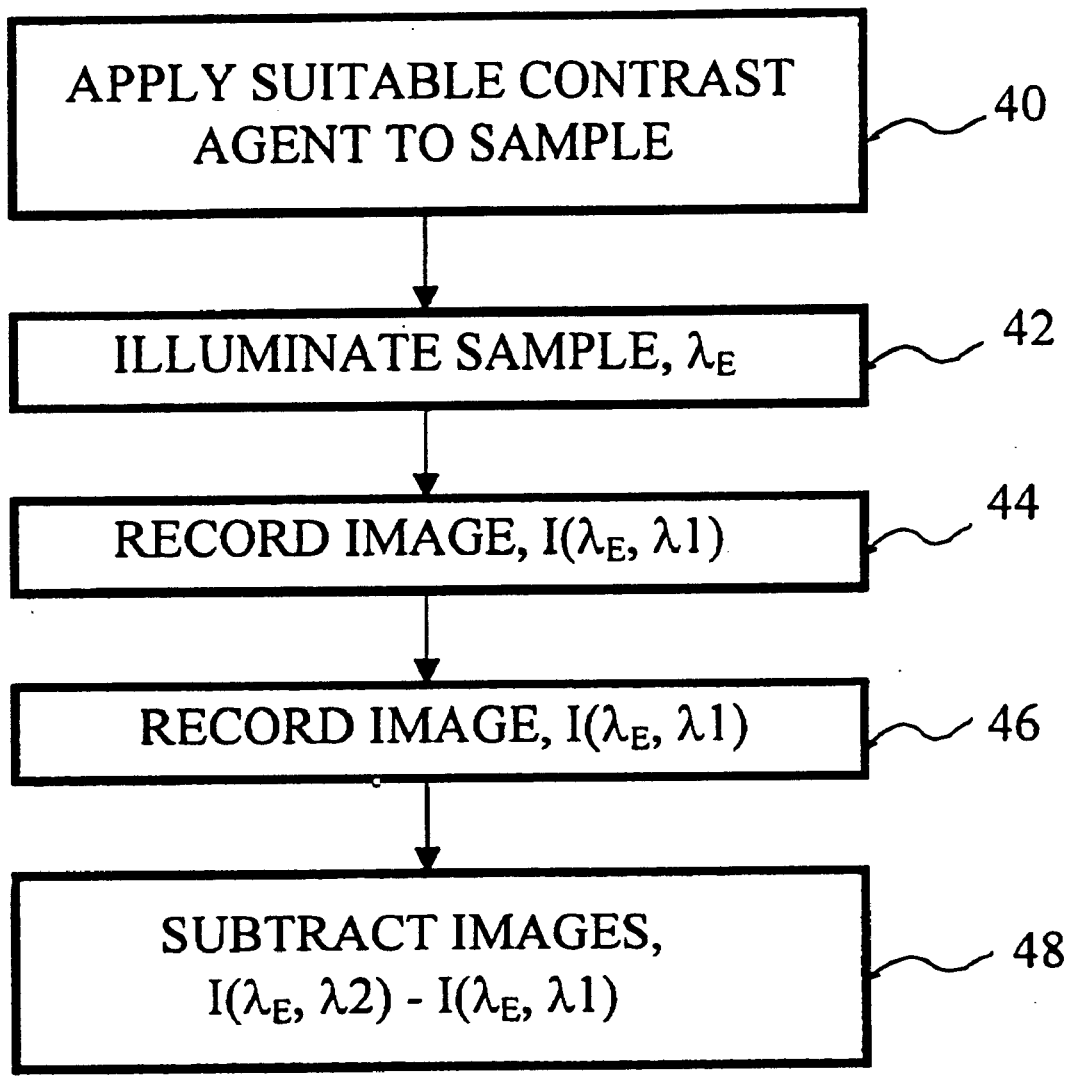
FIG. 4 is a flow chart illustrating an emission difference spectral imaging method in accordance with the present invention.
Figure 5:
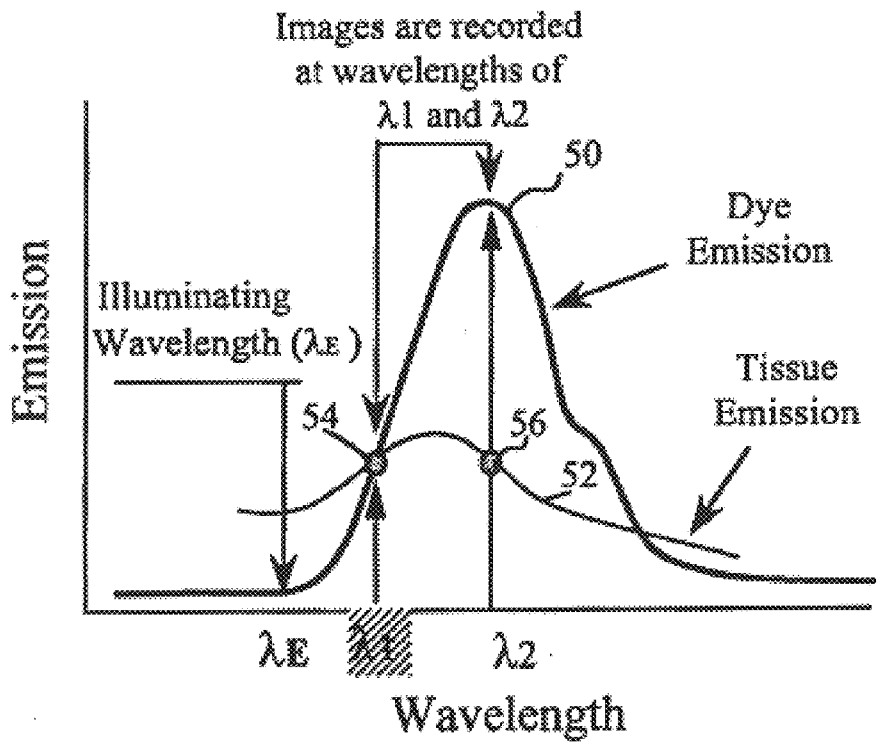
FIG. 5 is a pictorial diagram depicting an emission difference spectral imaging method, in accordance with the present invention.

FIG. 4 is a flow chart illustrating the steps involved in a first imaging method in accordance with the present invention. FIG. 5 is a pictorial diagram depicting the physical processes involved in the method of FIG. 4, referred to as the emission difference spectral imaging technique. First, a sample is treated with an appropriate contrast agent (step 40). The sample is then illuminated with monochromatic light at a selected wavelength, $\lambda_E$ (step 42). Light is absorbed by the tissue as well as the contrast agent. Two images of emissions from the energized sample are then recorded. The first image is taken with the detector 26 centered at wavelength $\lambda_1$ (step 44). The second image is taken with the detector centered at wavelength $\lambda_2$ (step 46). Preferably, narrow band filters 30 are interposed between the sample and the detector 26 to discriminate against all but the desired imaging wavelengths. The first and second images are then subtracted from one another (step 48) to provide an enhanced image signal. If necessary, an additional step of normalization can be performed on the first and second images prior to subtraction in order to further improve the imaging results.

Figures 5A, 5B, 5C:
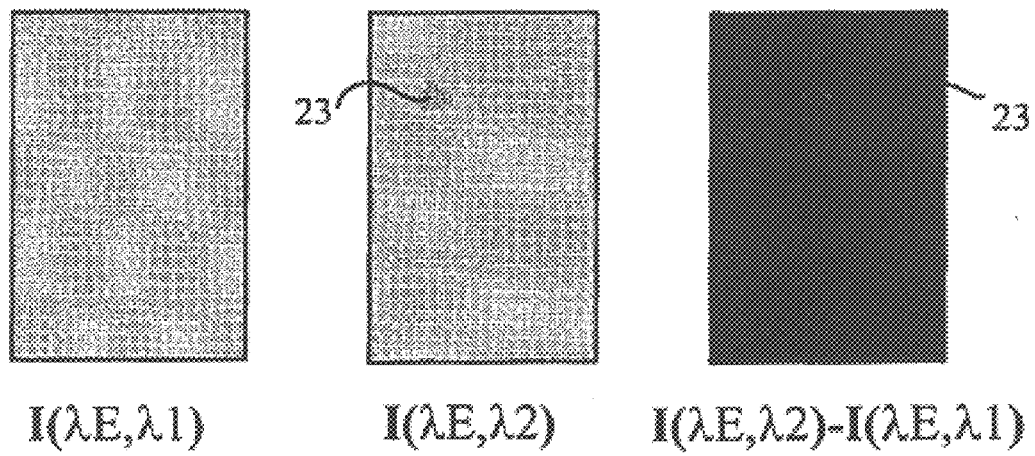
Figure 6:
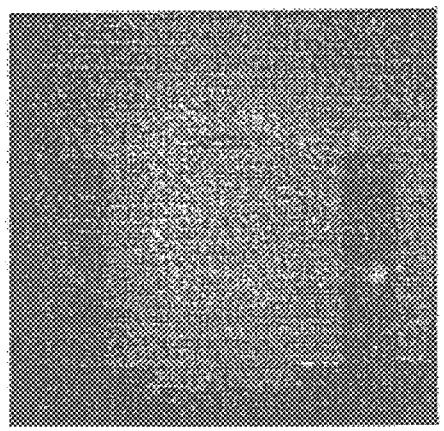
Figure 6:
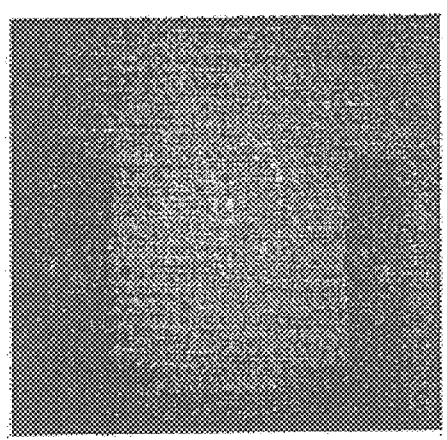
Figure 6:
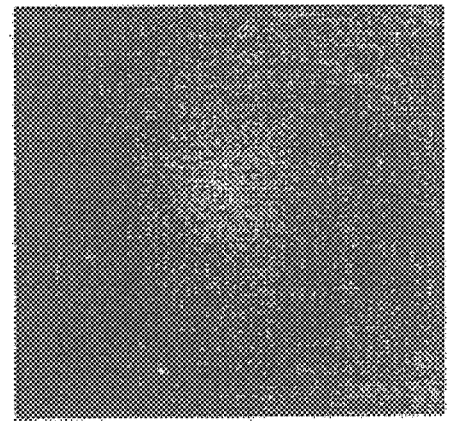

Wavelengths $\lambda_1$ and $\lambda_2$ are selected such that while the emissions by the contrast agent (luminous object) are very different at $\lambda_1$ and $\lambda_2$, the emissions by the tissue sample are approximately the same. This is illustrated in FIG. 5. Referring to FIGS. 6A–6C, the two images recorded $I(\lambda_E, \lambda_1)$ (FIG. 6A) and $I(\lambda_E, \lambda_2)$ (FIG. 5B) differ in the fact that the contribution in the image of the luminous object 23 is different and more specifically, in the image $I(\lambda_E, \lambda_2)$ of the luminous object is more "intense" than in the image $I(\lambda_E, \lambda_1)$ due to stronger emission by the dye at $\lambda_2$. The rest of the image is dominated by the emission from the tissue 22A and the presence of the image coming from the luminous object 23 may be hardly visible in either image. Subtraction of the two images (step 48) after normalization, so that the intensity of the emission by the tissue 22A is substantially equal in both images, leads to a new image (FIG. 6C). In FIG. 6C, the image component due to the tissue 22A is minimized and the dominant image feature becomes the emission by the luminous object 23.

The above described principals were applied to a tissue sample where the luminous object 23 (~1 mm diameter breast tissue lesion embedded in cardio green dye) is located 3.1 cm underneath the surface. For this example, the illumination wavelength was $\lambda_E$=630 nm, the first imaging wavelength was, $\lambda_1$=790 nm and the second imaging wavelength was, $\lambda_2$=830 nm. The reason for choosing these values of $\lambda_1$ and $\lambda_2$ is that while the intensity of the emission by the tissue at 790 and 830 nm is not very different (see FIG. 1), the intensity of the emission by the contrast agent is different by a factor of ~3. This allows for enhancement of the visibility of the luminous object after elimination of the contribution in the image component arising from tissue emission using subtraction of the images.

Figure 7:
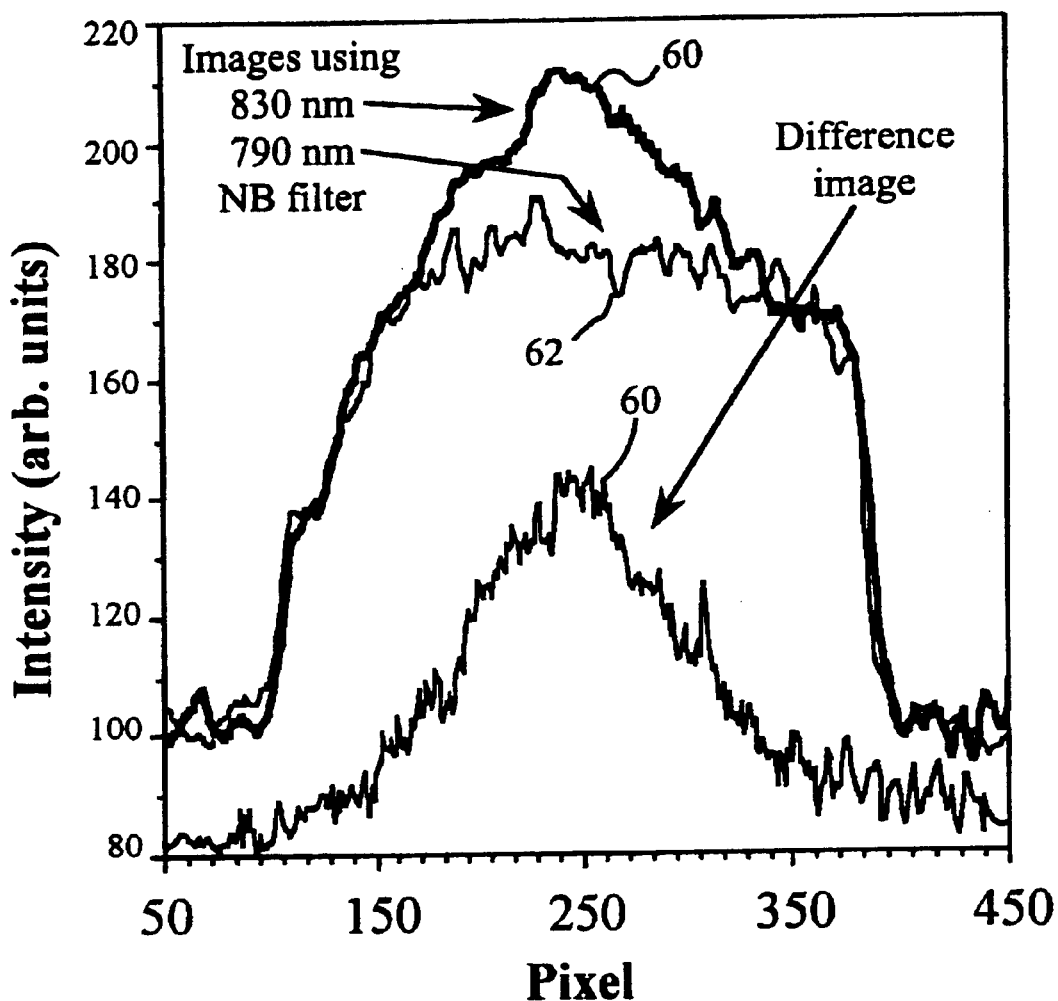
FIG. 7 is a graph of digitized image intensity profiles representing images obtained under 632 nm illumination for 790 nm imaging (middle profile), for 830 nm imaging (upper profile) and for the emission difference image (lower profile)

FIG. 7 is a graph illustrating the digitized intensity profiles across a one-pixel line crossing the luminous object 23 at its middle. The first graph line 60 corresponds to the image at 790 nm and the second graph line 62 corresponds to the image at 830 nm. The image arises predominantly from emission by the tissue and in a smaller part by the luminous object. The stronger emission by the luminous object contributes in a brighter image at 830 nm. Subtraction of the two images leads to the reduction of the contribution of the tissue and enhancement of the visibility of the luminous object. This is illustrated in graph line 64 where the digitized intensity profile of the difference image is shown.

Figure 8:
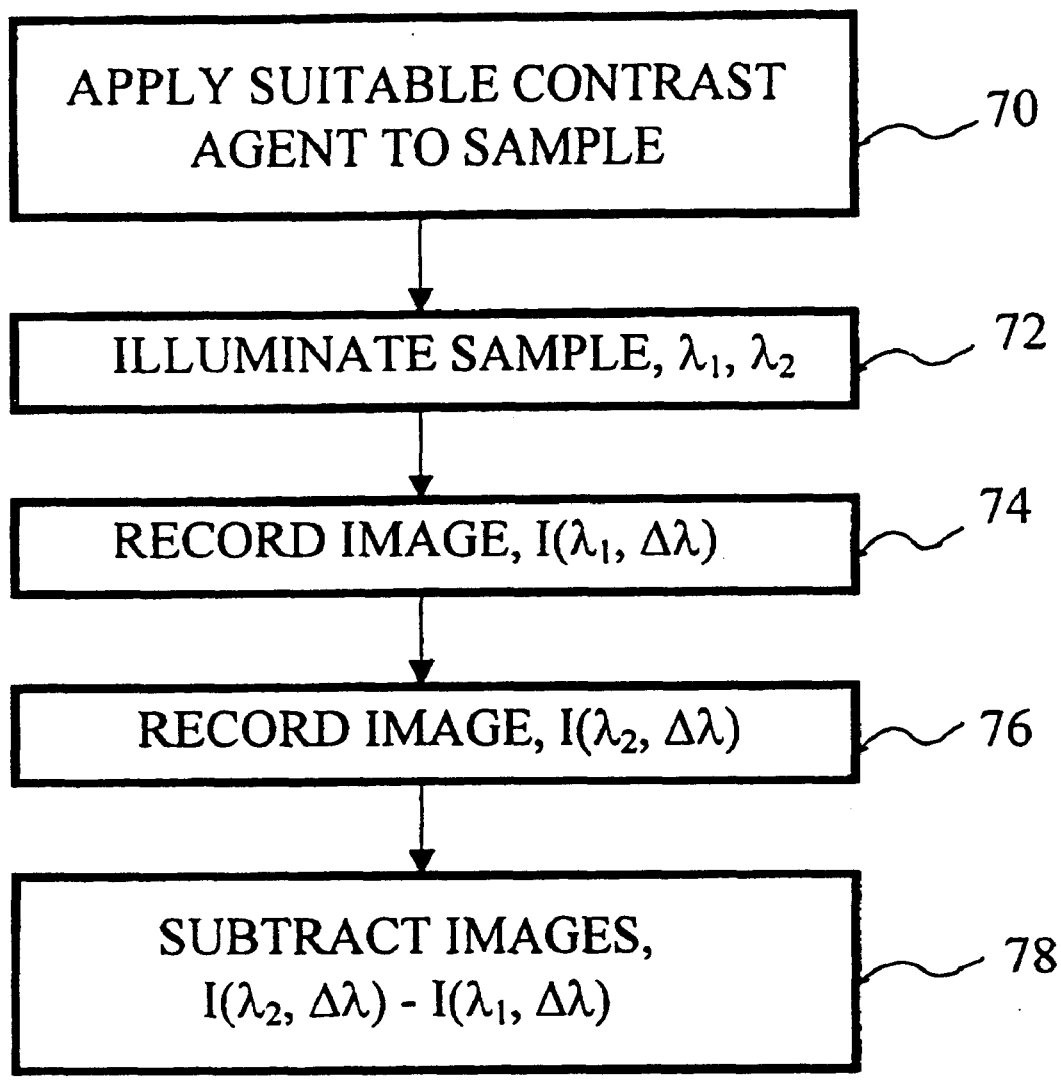
FIG. 8 is a flow chart illustrating an excitation difference spectral imaging method, in accordance with the present invention.
Figure 9:
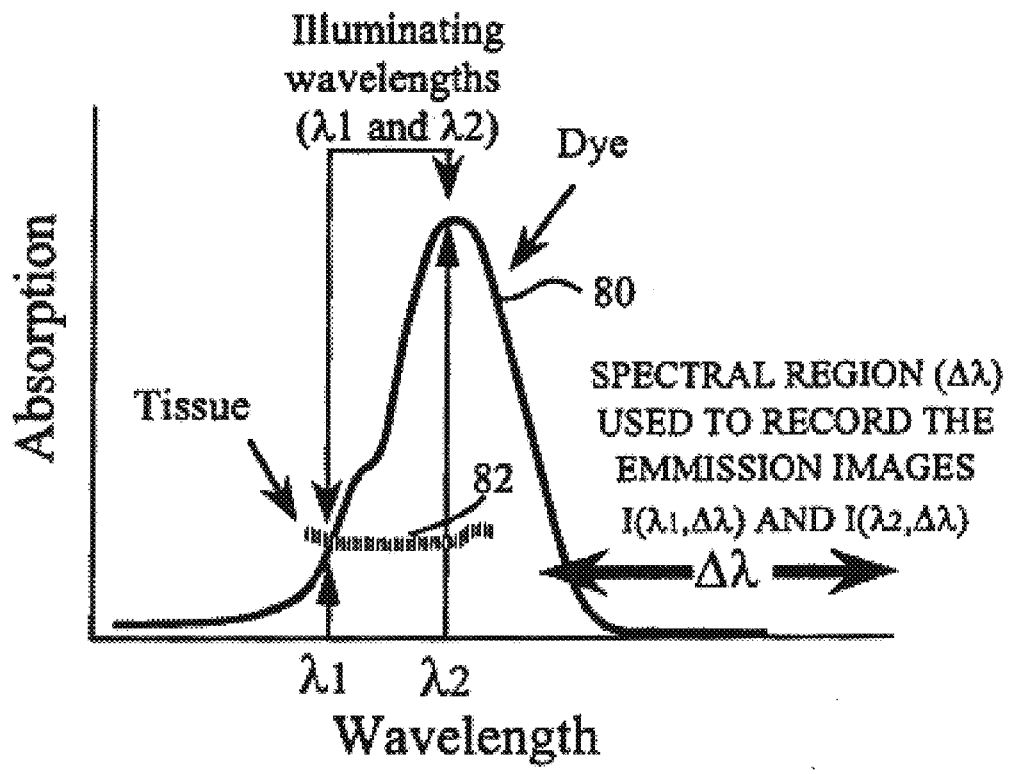
FIG. 9 is a pictorial diagram depicting an excitation difference spectral imaging method, in accordance with the present invention.
Figure 9A:
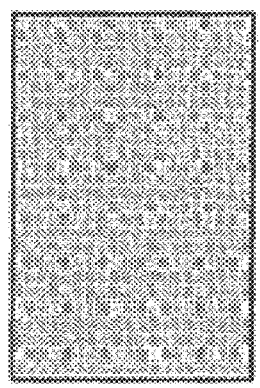
Figure 9B:
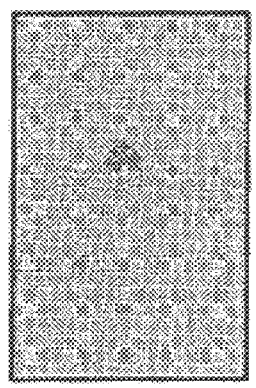
Figure 9C:
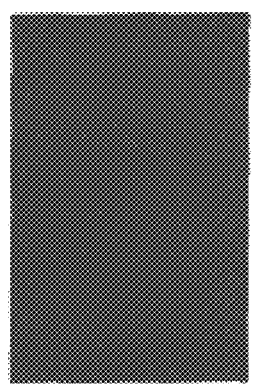

A second imaging method in accordance with the present invention, referred to as excitation spectral difference imaging, is illustrated in the flow chart of FIG. 8. FIG. 9 is a pictorial diagram depicting the physical principals yielding to the excitation spectral difference imaging technique of FIG. 8. Referring first to FIG. 8, the sample is treated with a contrast agent (step 70) and is then illuminated with monochromatic light at two different wavelengths $\lambda_1$ and $\lambda_2$ (step 72). A first image is recorded in a selected imaging band ($\Delta\lambda$) under $\lambda_1$ illumination as shown in FIG. 9a (step 74) and a second image is recorded in the selected imaging band ($\Delta\lambda$) under $\lambda_2$ illumination as shown in FIG. 9b (step 76). The two recorded images are then subtracted to form the resulting image as shown in FIG. 9c (step 78).

Figure 10:
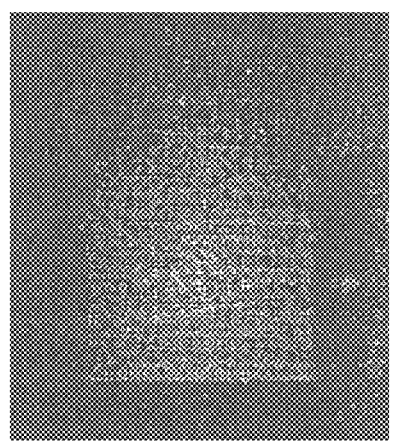
Figure 10:
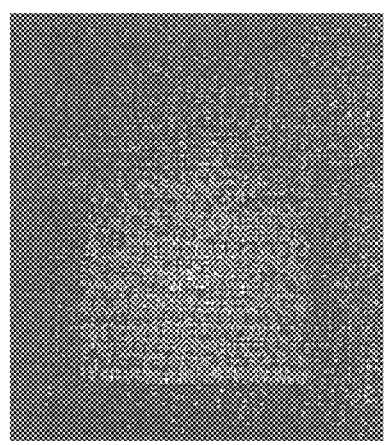
Figure 10:
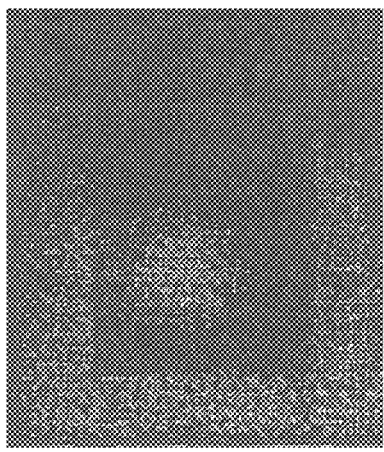

The wavelengths $\lambda_1$ and $\lambda_2$ are selected so that the absorption by the tissue is approximately the same for both wavelengths while the absorption by the contrast agent (luminous object) is very different at $\lambda_1$ and $\lambda_2$. Filter 30 (FIG. 2) which is positioned in front of the detector 26 takes the form of a bandpass filter so that the image is formed by emitted light only in the selected imaging band, $\Delta\lambda$. Referring to FIGS. 10A and 10B, the two images recorded $I(\lambda_1, \Delta\lambda)$ and $I(\lambda_2, \Delta\lambda)$ differ in the fact that the contribution in the image of the luminous object 23 is different and more specifically, in the image $I(\lambda_2, \Delta\lambda)$ the luminous object is "brighter" than in the image $I(\lambda_1, \Delta\lambda)$ due to stronger absorption and subsequent emission by the dye at $\lambda_2$ illumination. The images are dominated by the tissue emission and the presence of the image coming from the luminous object 23 may be hardly visible in both images. Subtraction of the two images, after normalization so that the intensity of the emission by the tissue is substantially equal in both images, leads to a new image (FIG. 10C) where the image component due to the tissue is substantially canceled out and the dominant feature becomes the emission by the luminous object 23.

Figure 11:
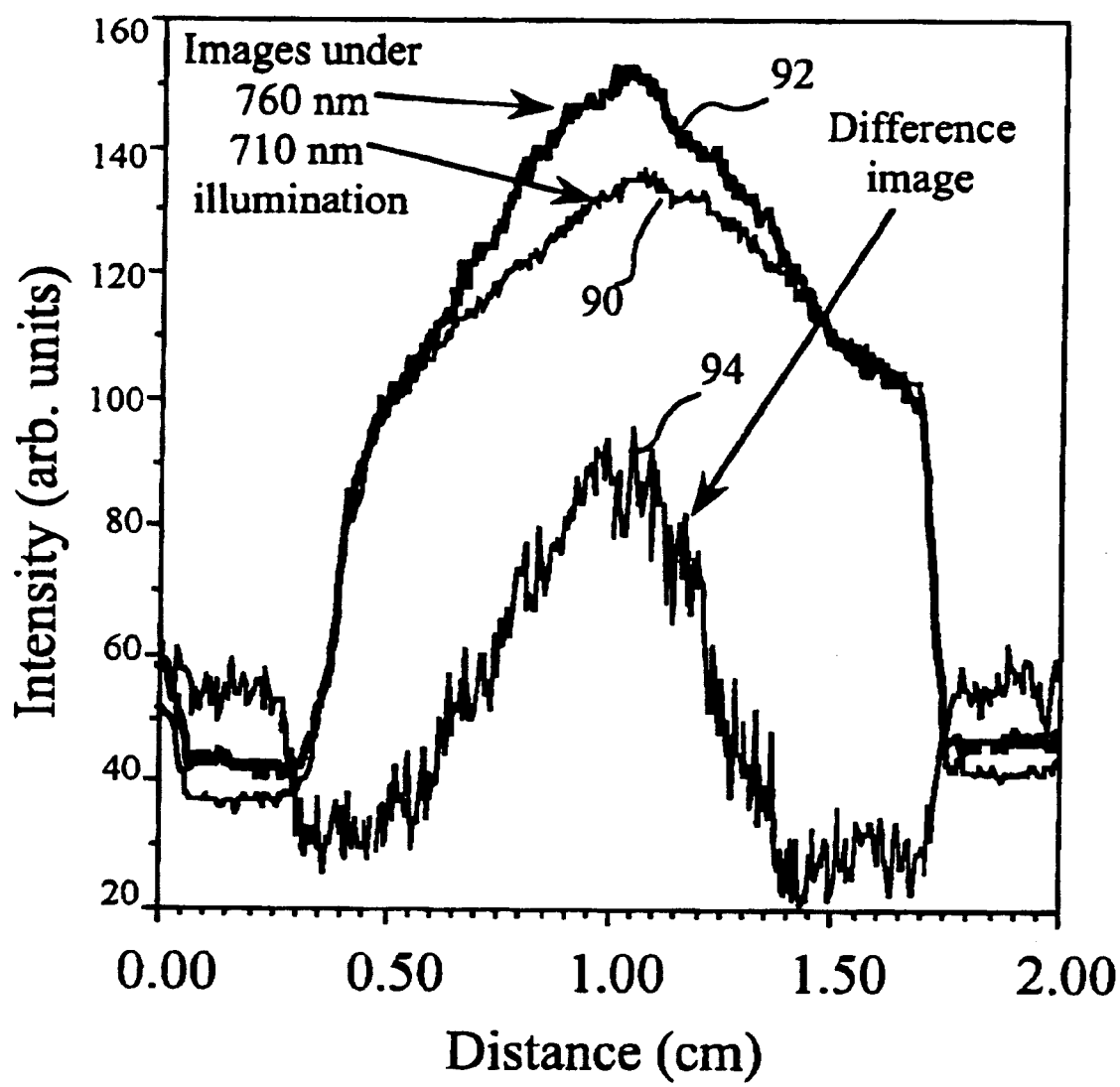
FIG. 11 is a graph of digitized image intensity profiles for images obtained under 710 nm illumination (middle profile), under 760 nm illumination (upper profile) and for the emission difference image (lower profile)

To demonstrate the principals described above, a tissue sample was imaged where the luminous object (~2 mm diameter breast tissue lesion embedded in cardio green dye) is located 1.5 cm underneath the surface. The wavelengths for illumination were $\lambda_1$=710 nm and $\lambda_2$=760 nm. An 830 nm long-pass filter was positioned in front of the detector 26 so that only photons with wavelength longer that ~800 nm are recorded to form the image. The reason for choosing these values of $\lambda_1$ and $\lambda_2$ is that while the absorption by the tissue at 710 and 760 nm is not very different, the absorption by the dye and subsequent emission by the luminous object is different by a factor of ~2 (see FIG. 3B). FIG. 11 is a graph illustrating digitized intensity profiles across a one-pixel line crossing the luminous object 23 at its middle under 710 nm illumination 90 and 760 nm illumination 92. The enhanced emission by the luminous object 23 under 760 nm illumination which is due to the enhanced absorption, contributes in a brighter image as shown in the intensity profile graph 92. Subtraction of the two images leads to a significant reduction from the contribution of the tissue as well as significant enhancement of the visibility of the luminous object. This is demonstrated in graph line 94 where the digitized intensity profile of the difference image is shown.

The imaging methods of the present invention help to increase the visibility of a luminous object located inside tissue. The overall result is significant improvement of the visibility and image quality of the luminous object 23 which is achieved by substantially reducing the image contribution of the tissue. In turn, the detection of luminous objects indicates the presence of diseases as targeted by a selected contrast agent. Many applications can take advantage of the benefits provided using this technique. A practical application of the present invention is its use for medical imaging. For example, specially made contrast agents can be used to detect cancers (in breast, gland, brain, liver, kindly, prostate and pancreas) and detect other disease (such as for Huntington's disease, Alzheimer, epilepsy, and diabetes) if selected dyes prefer to be located in such tumors, i.e. HPD, or disease genes or molecules. The dye will be administrated to the patient and it will be concentrated in the specified diseased area. Emission from the contrast agent (dye) will show the presence of the diseased tissue and using the methods of the present invention, an image of the diseased tissue will be obtained.

The light emitted by the luminous object 23 may be imaged by the detector 26 at any angle with respect to the illumination and independently of the way the luminous object was photo excited. The back scattering geometry utilized in FIG. 2 was employed because at the present time we believe is the potentially most useful.

Figure 12A:
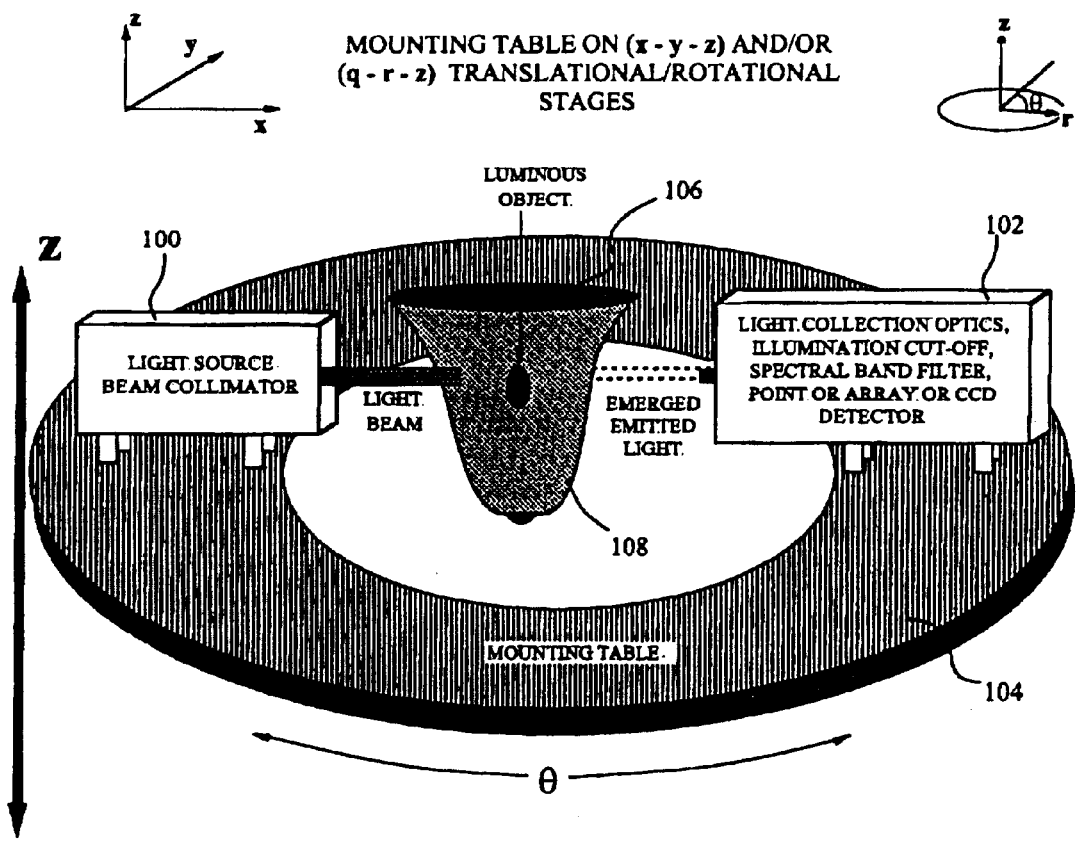
FIGS. 12A and 12B are pictorial diagrams in a perspective view and top view, respectively, of an apparatus for imaging/detecting a luminous object located inside tissue formed in accordance with the present invention.
Figure 12B:
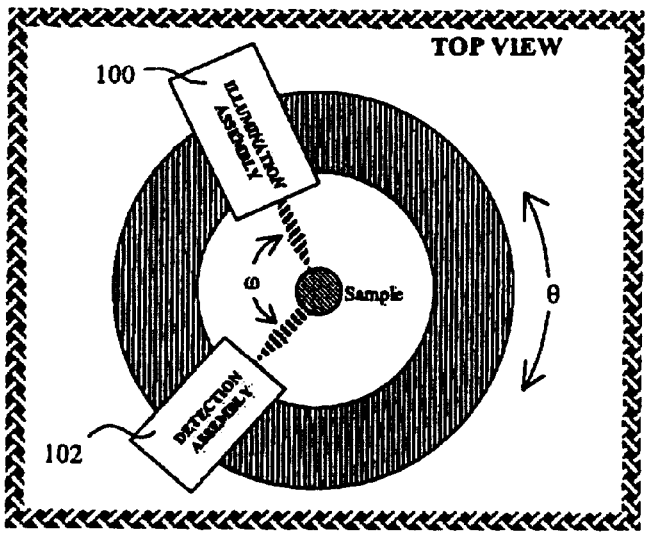

A transillumination imaging apparatus can also be used for some applications, such as breast imaging. FIGS. 12A and 12B illustrate an apparatus formed in accordance with the present invention which is suitable for such detection/imaging applications. Referring to FIG. 12A, the imaging system includes an illumination source 100 and a detector 102, each fixedly mounted on a platform 104 with respect to one another. The illumination source 100 and detector 102 include the previously discussed filters and optics and are substantially similar to that discussed in detail in connection with FIG. 2. The illumination source 100 and detector 102 are arranged such that a specimen 106 to be imaged can be interposed between them. The illumination source 100 can be placed in direct opposition to the detector 102 for transillumination or the illumination source 100 and detector 102 can be offset at an angle, ω, as illustrated in FIG. 12B. The platform 104 is equipped for rotational motion about a Z-axis of the specimen 106.

As the platform rotates, images are taken in accordance with the previously disclosed methods over a 360° rotation. Either the excitation and/or emission spectral difference imaging methods may then be used to cancel out the image component arising from the tissue to enhance the visibility of the luminous object associated with the diseased part of the body. The resolution of the image of the luminous object 108 depends on the scattering due to the mass and size of the section of the tissue positioned between the detector 102 and the luminous object. If the object is deep inside the tissue, the image resolution will be poor. In this case, the most important information obtained will be the detection of the presence of the luminous object.

The methods described above can be used with small modifications for detection rather than imaging of the presence of a luminous object in tissue. In this arrangement, the objective is to scan the sample (human body or human organ) in a point by point or over area method and determine if a luminous object is located inside the sample. This method is substantially similar to the imaging method described above with the only difference that the detector 102 will take the form of a one dimensional detector (photodiode or photomultiplier) or an array detector, rather than a CCD camera. The detector will record the emitted light and obtain readings for two emitted wavelengths under the same illumination wavelength for the emission spectral difference detection method. Alternatively, the detector will record two readings of the emitted light at the same spectral band for two different excitation wavelengths for the excitation spectral difference detection scheme. Subtraction of the two more readings after normalization will cancel out the contribution in the signals of the light emitted by the tissue and allow for a reading of the light emitted by the luminous object. These detection schemes will allow detection of the presence of a luminous object in the form of a positive or negative answer. An array detector may be used in a slightly different arrangement in order to replace the two-dimensional point by point scanning with a one dimensional scanning while the other dimension will be covered by the array detector.

In the imaging or detection schemes described above, the illumination light may by delivered using a fiber. In addition, the image may be transferred to the detector using an imaging fiber bundle, an endoscope or an image preserving waveguide. As an example, a prostate may be illuminated using a fiber reaching near or inside prostate using the urinary system or the rectum while the image is obtained outside the body. Alternatively, an imaging fiber probe reaching near prostate through the rectum may my used to capture and transfer the image in the CCD detector. As a result, using the appropriate light delivery and image acquisition schemes, most of the human body can be scanned.

Figure 13:
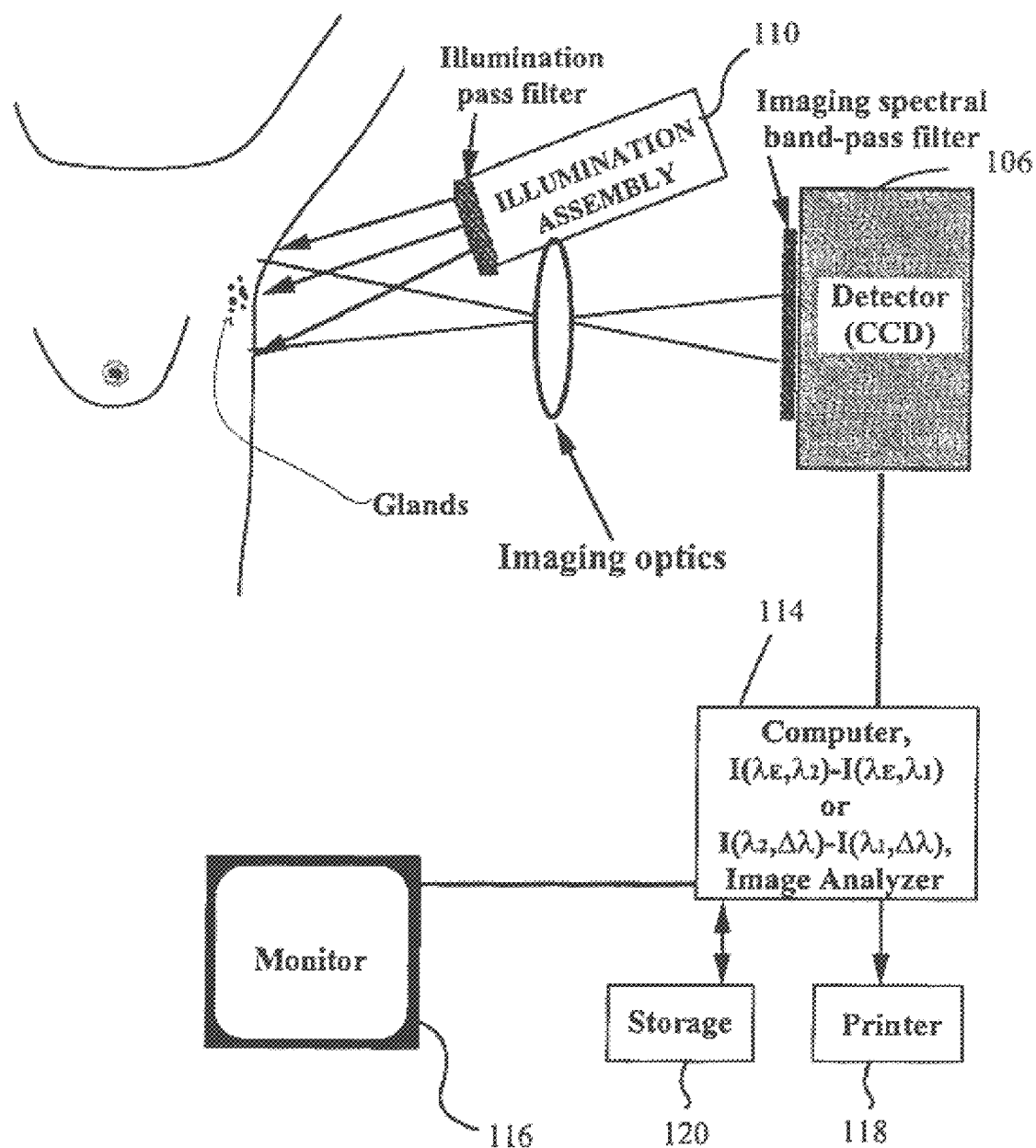
FIG. 13 is a pictorial diagram of an apparatus for imaging glands located under the arm, formed and operated in accordance with the present invention.

For example, FIG. 13 illustrates an exemplary imaging system for screening the glands located under the arm of a human being. This embodiment is substantially similar to that disclosed in FIG. 2, wherein the illumination assembly 110, detector 112, and associated filters and optics are arranged in a back scattering configuration. The illumination assembly 110 provides an illumination beam which is directed to the underarm region and the emissions from the glands, treated with an appropriate contrast agent, are received by the detector assembly 112. The detected image signals are presented to an image processing system 114 operating in accordance with either the excitation and/or emission spectral difference imaging methods of the present invention to enhance the visibility of a luminous object associated with the glands being screened. Once appropriately processed, the image signals are presented on a suitable display monitor 116. The images can also be output on a suitable printer 118 or presented to digital storage 120, for future use.

FIGS. 14A and 14B illustrate an application of the present invention to an imaging system formed with an endoscope for imaging of internal organs and the like. In this embodiment, an illumination source 121 is coupled through suitable illumination filters 122 to a flexible fiber optic cable 124. The fiber optic cable 124 is coupled into and through a central bore of an endoscope 126. Referring to FIG. 14B, an image collecting fiber-bundle 126 is also included in the central bore of the endoscope 128, This fiber-bundle 126 receives illumination signals from the tissue sample and presents these signals to a detector assembly 112. The detected image signals are presented to an image processing system 114 operating in accordance with either the excitation and/or emission spectral difference imaging methods to enhance the visibility of a luminous object associated with the glands being screened. Once appropriately processed, the image signals are presented on a suitable display monitor 116. The images can also be output on a suitable printer 118 or presented to digital storage 120, for future use.

Figure 15A:
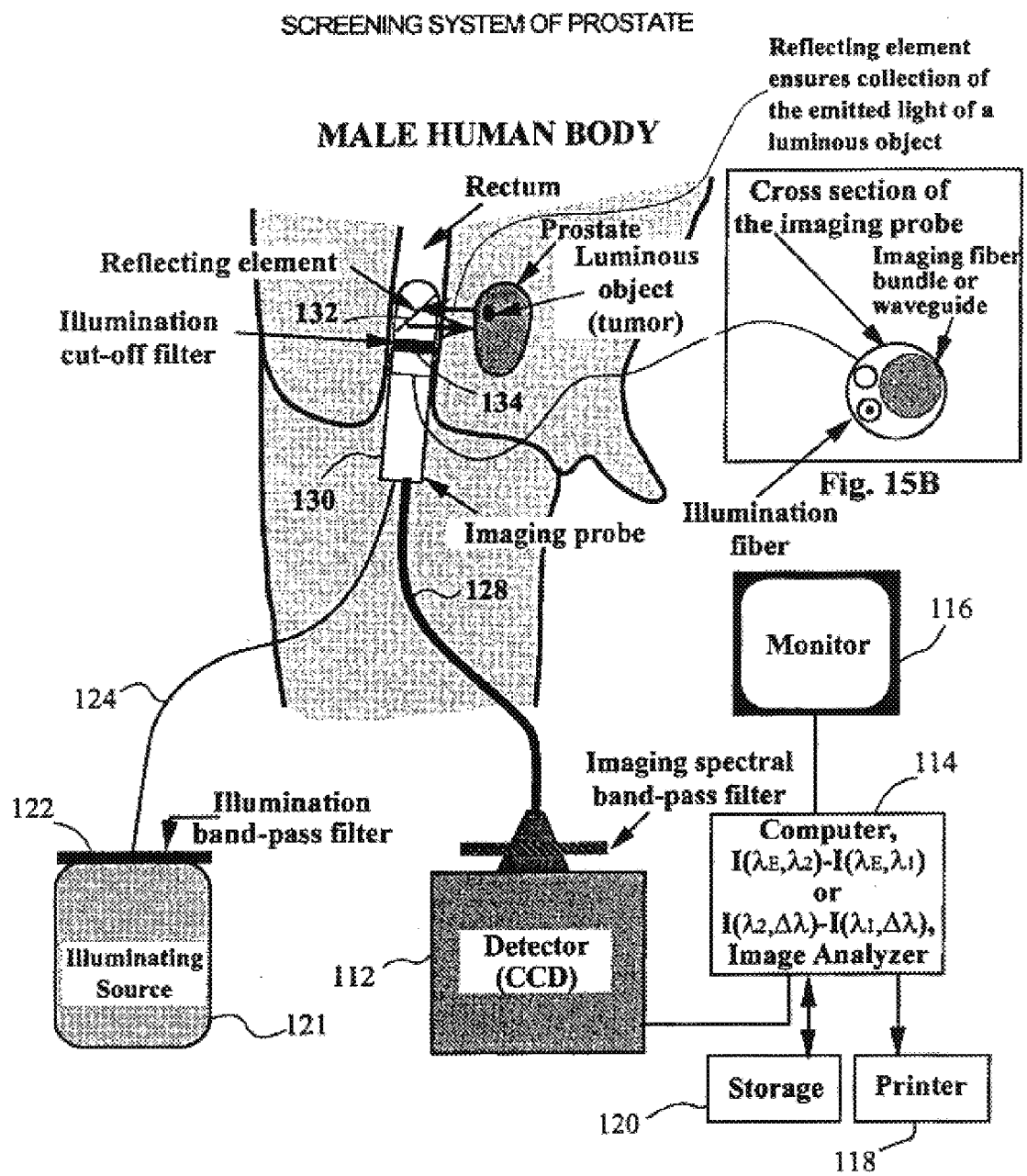
FIG. 15A is a pictorial diagram of an apparatus for imaging a prostate, formed and operated in accordance with the present invention.

FIGS. 15A and 15B illustrate an imaging system of the present invention particularly well suited for prostate screening. The system includes an illumination source 121 coupled through suitable illumination filters 122 to a flexible fiber optic cable 124. The fiber optic cable 124 is coupled to an imaging probe body 130 which is suitably formed for insertion into the rectum of a patient. The light from the illumination source is directed to the area where a luminous body may reside through suitable optics, such as a reflecting element 132. The emissions from the prostate are incident upon the reflecting element 132 and are presented to an imaging fiber-bundle 128 which is within the imaging probe body 130. Preferably, an illumination cut off filter 134 is interposed between the optics and the imaging fiber-bundle 128. The imaging fiber-bundle 128 transports the received image signals to an appropriate detector 112. The image signals from the detector 112 are then processed in a manner previously discussed.

Figure 16:
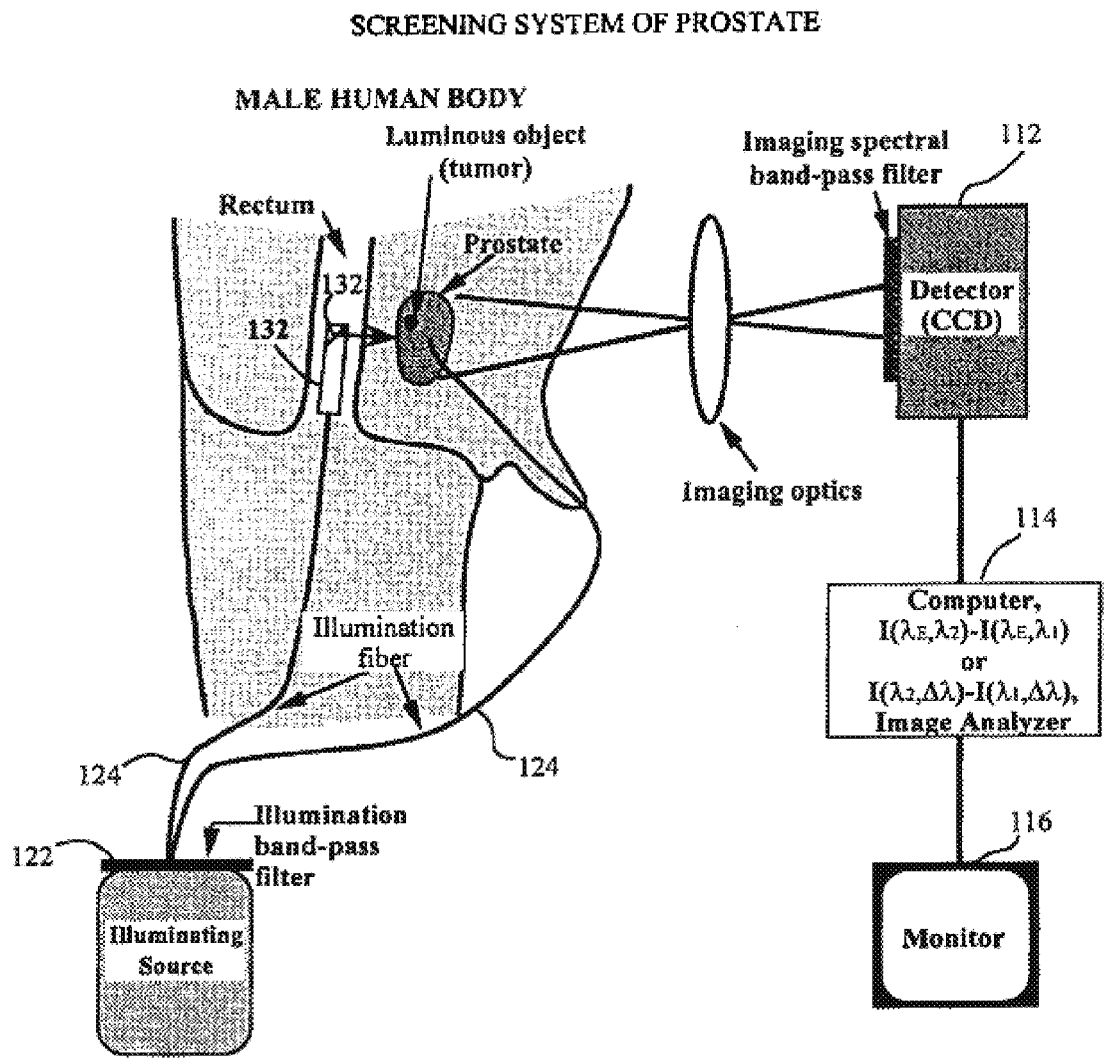
FIG. 16 is a pictorial diagram of an alternate embodiment of an apparatus for imaging a prostate, formed and operated in accordance with the present invention.

As an alternate embodiment of the prostate screening apparatus, the illumination fiber 124 need not be coupled to the imaging probe body 130. For a transillumination application, the illumination fiber 124 may be separately inserted into the urinary system. Similarly, the detection fiber-bundle 128 can be removed from the imaging probe body 130, and the detector 112 and suitable optics can be placed outside the body, as illustrated in FIG. 16. The emissions from the luminous object and tissue are then collected by appropriate optical elements (lenses and/or mirrors) located outside the body and directed into a detector 112.

Having described preferred embodiments of the present invention, it is noted that various modifications and variations can be made by persons skilled in the art in light of the above teachings. It is therefore to be understood that changes may be made to the particular embodiments disclosed which are within the scope and spirit of the invention as outlined by the appended claims.

What is claimed is:

1. An imaging system which enhances the visibility of an object located inside tissue, comprising:
   means for providing a single contrast agent into said object causing the object to become a luminous object;
   means for illuminating the tissue and said luminous object;
   means for detecting a first image signal emitted having a first emission intensity from said contrast agent in said luminous object at a first imaging wavelength;
   means for detecting a second image signal emitted having a second emission intensity from said contrast agent in said luminous object at a second imaging wavelength, wherein emissions from said contrast agent are substantially dissimilar at said first and second image wavelengths and emissions from said tissue are substantially similar at said first and second image wavelengths and wherein said substantially dissimilar emissions from said contrast agent are determined by said first and second imaging wavelengths; and
   means for performing normalization and subtraction of said detected image signals, whereby a new image signal is generated in which an image of the luminous object is enhanced.

2. The imaging system as defined by claim 1, wherein said means for illuminating the tissue and said luminous object include a substantially monochromatic light source operating at a selected illumination wavelength.

3. The imaging system as defined by claim 2, wherein said means for illuminating the tissue and said luminous object further comprises a flexible illumination fiber operatively coupled to said monochromatic light source, said fiber transporting said illumination to a selected area of tissue.

4. The imaging system as defined by claim 1, wherein said means for detecting said first and second image signals includes a photo detector.

5. The imaging system as defined by claim 4, wherein said photodetector includes a CCD detector.

6. The imaging system as defined by claim 4, wherein said means for detecting said first and second image signals further comprises a detector fiber bundle, said detector fiber bundle transporting said first and second image signals from an area of tissue to said photo detector.

7. The imaging system as defined by claim 6, further comprising means for displaying said image signals.

8. The imaging system as defined by claim 7, further comprising means for storing said image signals.

9. The imaging system as defined by claim 6, further comprising means for printing said image signals.

10. The imaging system as defined by claim 1, further comprising:
    an endoscope, said endoscope having a central bore therein, and wherein said means for illuminating the tissue and said luminous object comprises:
    a substantially monochromatic source operating at a selected illumination wavelength; and
    a flexible illumination fiber operatively coupled to said source, said fiber transporting said illumination through said endoscope central bore to a tip of said endoscope.

11. The imaging system as defined by claim 10, wherein said means for detecting first and second image signals comprises:
    a photo detector, and
    a detector fiber bundle, said detector fiber bundle transporting image signals from said tip and through said central bore in said endoscope to said photo detector.

12. The imaging system as defined by claim 1, further comprising a rotatable platform, said means for illuminating the tissue and said luminous object and said means for detecting first and second image signals being mounted to said rotatable platform.

13. An imaging system which enhances the visibility of an object located inside tissue, comprising:
    means for applying a single contrast agent to the tissue, thereby staining the object;
    means for selecting at least one illuminating wavelength;
    means for illuminating the tissue at said selected illuminating wavelength;
    means for selecting a plurality of imaging wavelengths;
    means for detecting a first fluorescence image signal emitted from said stained object having a first emission intensity at a first image wavelength and a second fluorescence image signal emitted from said stained object having a second emission intensity at a second image wavelength, wherein emissions from said contrast agent are substantially dissimilar at said first and second image wavelengths and emissions from said tissue are substantially similar at said first and second image wavelengths and wherein said substantially dissimilar emissions from said contest agent are determined by said first and second imaging wavelengths; and means for performing normalization and subtraction of said detected image signals, whereby a new image signal is generated in which an image of the stained object is enhanced.

14. A method for imaging an object located inside tissue comprising the steps:

applying a single contrast agent to the object, whereby the object becomes a luminous object;

illuminating the tissue and said object at a selected wavelength;

recording fire signals having a first emission intensity at a first imaging wavelength;

recording second signals having a second emission intensity at a second imaging wavelength, wherein emissions from said contrast agent are substantially dissimilar at said first and second imaging wavelengths and emissions from said tissue are substantially similar at said first and second imaging wavelengths and wherein said substantially dissimilar emissions from said contrast agent are determined by said first and second imaging wavelengths; and subtracting said first signals from said second signals, whereby an image component resulting from the tissue is minimized while an image component resulting from said luminous object is enhanced.

15. The method as defined by claim 14, wherein said first imaging wavelength and said second imaging wavelength are selected such that spectral emission characteristics of the tissue are substantially constant while spectral emission characteristics of said illuminated object are substantially different.

16. The method as defined by claim 15, further comprising a step of normalizing said recorded signals prior to said subtracting step.

17. The method as defined by claim 16, wherein the tissue is one of human breast, brain, prostate, liver, kidney and pancreas.

18. The method as defined by claim 17, wherein said tissue is one of a human breast, brain, prostate, liver, kidney and pancreas.

19. The method as defined by claim 18, wherein said selected illumination wavelength is in the range of 700 to 1200 nanometers.

* * * * *